United States Patent
Edwards et al.

(10) Patent No.: US 6,419,673 B1
(45) Date of Patent: *Jul. 16, 2002

(54) ABLATION OF RECTAL AND OTHER INTERNAL BODY STRUCTURES

(75) Inventors: Stuart D. Edwards, Portola Valley; Steven V Marcus, Los Altos, both of CA (US)

(73) Assignee: Stuart Edwards, Corral De Tierra, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/557,993

(22) Filed: Apr. 25, 2000

Related U.S. Application Data (63) Continuation of application No. 08/717,612, filed on Sep. 20, 1996, now Pat. No. 6,077,257, and a continuation-in-part of application No. 08/660,539, filed on Jun. 7, 1996, now Pat. No. 5,743,904, and a continuation-in-part of application No. 08/663,004, filed on Jun. 7, 1996, now abandoned, and a continuation-in-part of application No. 08/651,800, filed on May 22, 1996, now Pat. No. 5,836,906, and a continuation-in-part of application No. 08/651,378, filed on May 22, 1996, now Pat. No. 5,738,114, and a continuation-in-part of application No. 08/651,796, filed on May 22, 1996, now abandoned, and a continuation-in-part of application No. 08/651,798, filed on May 22, 1996, now abandoned, and a continuation-in-part of application No. 08/643,203, filed on May 6, 1996, now Pat. No. 5,718,702, and a continuation-in-part of application No. 08/643,524, filed on May 6, 1996, now Pat. No. 5,743,870.

(51) Int. Cl.[7] ............................................. A61B 18/18
(52) U.S. Cl. ........................ 606/41; 607/101; 607/133
(58) Field of Search .................... 606/41, 42, 45–50; 607/101–105, 133

(56) References Cited

U.S. PATENT DOCUMENTS

| | | | |
|---|---|---|---|
| 5,334,193 A | * 8/1994 | Nardella | 606/41 |
| 5,370,675 A | * 12/1994 | Edwards et al. | 607/101 |
| 5,505,730 A | 4/1996 | Edwards | |
| 5,575,788 A | * 11/1996 | Baker et al. | 606/41 |
| 5,688,267 A | * 11/1997 | Panescu et al. | 606/31 |
| 5,709,224 A | * 1/1998 | Behl et al. | 128/898 |
| 6,006,755 A | * 12/1999 | Edwards | 128/898 |
| 6,009,877 A | 1/2000 | Edwards | |
| 6,077,257 A | 6/2000 | Edwards et al. | |

* cited by examiner

Primary Examiner—Michael Peffley
(74) Attorney, Agent, or Firm—Michael A. Glenn; Christopher Peil (57) ABSTRACT

The invention provides an apparatus and system for ablation of body structures or tissue in the region of the rectum. A catheter is inserted into the rectum, and an electrode is disposed thereon for emitting energy. The environment for an ablation region is isolated or otherwise controlled by blocking gas or fluid using a pair of inflatable balloons at upstream and downstream locations. Inflatable balloons also serve to anchor the catheter in place. A plurality of electrodes are disposed on the catheter and at least one such electrode is selected and advanced out of the catheter to penetrate and ablate selected tissue inside the body in the region of the rectum. The electrodes are coupled to sensors to determine control parameters of the body structure or tissue, and which are used by feedback technique to control delivery of energy for ablation or fluids for cooling or hydration. The catheter includes an optical path disposed for coupling to an external view piece, so as to allow medical personnel to view or control positioning of the catheter and operation of the electrodes. The catheter is disposed to deliver flowable substances for aiding in ablation, or for aiding in repair of tissue, such as collagen or another substance for covering lesions or for filling fissures. The flowable substances are delivered using at least one lumen in the catheter, either from at least one hole in the catheter, from an area of the catheter covered by a microporous membrane, or from microporous balloons.

40 Claims, 5 Drawing Sheets

ABLATION OF RECTAL AND OTHER INTERNAL BODY STRUCTURES

CROSS-REFERENCE TO RELATED APPLICATIONS

This application is a continuation of co-pending Application Ser. No. 08/717,612, filed Sept. 20, 1996, now U.S. Pat. No. 6,077,257 in the name of Stuart D. Edwards and Steven Marcus, titled "Ablation of Rectal and Other Internal Body Structures,"

This application is a continuation-in-part of the following co-pending applications:

application Ser. No. 08/651,800, filed May 22, 1996, now U.S. Pat. No. 5,836,906;

application Ser. No. 08/651,378, filed May 22, 1996, now U.S. Pat. No. 5,738,114;

application Ser. No. 08/643,203, filed May 6, 1996, now U.S. Pat. No. 5,718,702;

application Ser. No. 08/643,524, filed May 6, 1996, now U.S. Pat. No. 5,743,870;

application Ser. No. 08/651,976, filed May 22, 1996, now abandoned;

application Ser. No. 08/651,798, filed May 22, 1996, now abandoned;

application Ser. No. 08/660,539, filed Jun. 7, 1996, now U.S. Pat. No. 5,743,904; and application Ser. No. 08/663,004, filed Jun. 7, 1996, now abandoned.

Inventions described herein can be used in combination or conjunction with inventions described in the following patent application:

application Ser. No. 09/407,658, filed Sept. 28, 1999, in the name of Stuart D. Edwards, titled "Treatment of Urinary Incontinence and Other Disorders by Application of Energy and Drugs," which application was a continuation of then co-pending application Ser. No. 08/677,811, filed Jul. 10, 1996, in the name of Lawrence J. Mohr, Jr., and Stuart D. Edwards, titled "Treating Aneurysms by Applying Hardening/Softening Agents to Hardenable/Softenable Substances," and which issued as U.S. Pat. No. 5,921,954 on Jul. 13, 1999;

Each of these applications is hereby incorporated by reference as if fully set forth herein.

BACKGROUND OF THE INVENTION

1. Field of The Invention

This invention relates to ablation of rectal and other internal body structures.

2. Description of Related Art

Human beings are subject to a number of disorders in the area of the rectum and colon, including hemorrhoids (external and internal), prolapse of the rectal muscles, rectal muscle spasms, anal fissures, polyps, diverticulosus and diverticulitus, and pilonital cysts. Other internal disorders in nearby regions of the body include (in men) prostate cancer, (in women) incontinence, vaginal bleeding, vaginal cysts, vaginal fibroids, prolapse of the uterus, and related tumors or cancerous tissue.

Although there are treatments available for these disorders, such as surgery, systemic or topical medication, these treatments suffer from various drawbacks, including (for surgery) their relative invasiveness and expense, and (for medicinal approaches) their relative ineffectiveness and the causation of serious side-effects. Accordingly, it would be advantageous to provide methods and apparatus for treatment which are not subject to the drawbacks of surgery and medicinal approaches.

Although it is known to use RF energy to ablate tissue in the body (such as heart muscle tissue) to treat disorders, one problem which has arisen in the art is accounting for the flow of bodily fluids and gases while ablating tissue. Bodily fluids can dissipate, and can detrimentally absorb, energy to be applied to tissue.

Accordingly, it would be advantageous to provide improved techniques for treatment of disorders in the area of the rectum and colon. This advantage is achieved by a method and system according to the present invention in which a catheter is inserted into the rectum, and at least one electrode is disposed thereon for emitting energy to ablate body structures or other tissue in an ablation region in or near the rectum, such as the sphincter, rectum, colon, or prostate.

SUMMARY OF THE INVENTION

The invention provides a method and system for ablation of body structures or tissue in an ablation region in or near the rectum (such as the sphincter, rectum, colon, or prostate). A catheter is inserted into the rectum, and at least one electrode is disposed thereon for emitting energy to ablate body structures or other tissue, such as by cell death, dehydration, or denaturation. The environment for the ablation region is isolated or otherwise controlled, such as by blocking gas or fluid using a pair of inflatable balloons at upstream and downstream locations from the ablation region. In a preferred embodiment, inflatable balloons also serve to anchor the catheter in place and prevent the catheter from being expelled from the body.

In preferred embodiments, the catheter is flexible for reaching a selected internal organ or region, a plurality of electrodes are disposed on the catheter and at least one such electrode is selected and advanced out of the catheter to penetrate and ablate selected tissue inside the body in ablation region in or near the rectum, such as an individual cyst, hemorrhoid, polyp, tumor, or other selected lesion or tissue. The electrodes are coupled to sensors to determine control parameters of the body structure or tissue, such as impedance or temperature, and which are used by feedback technique to control delivery of energy for ablation or fluids for cooling or hydration. In a preferred embodiment, the catheter includes an optical path disposed for coupling to an external view piece, so as to allow medical personnel to view or control positioning of the catheter and operation of the electrodes.

In further preferred embodiments, the catheter is disposed to deliver flowable substances for aiding in ablation, such as saline or antibiotics, or for aiding in repair of tissue (either before or after ablation), such as collagen or another substance for covering lesions or for filling fissures in or near the ablation region, or for other medicinal effects, such as anesthetic, anti-inflammatory, or antispasmodic substances. The flowable substances are delivered using at least one lumen in the catheter, either from at least one hole in the catheter, from an area of the catheter covered by a microporous membrane, or from microporous balloons (either the same as or in addition to balloons used to anchor the catheter in place or to block gas or fluid).

DESCRIPTION OF THE PREFERRED EMBODIMENT

CATHETER AND ELECTRODE ASSEMBLY

Figure 1:
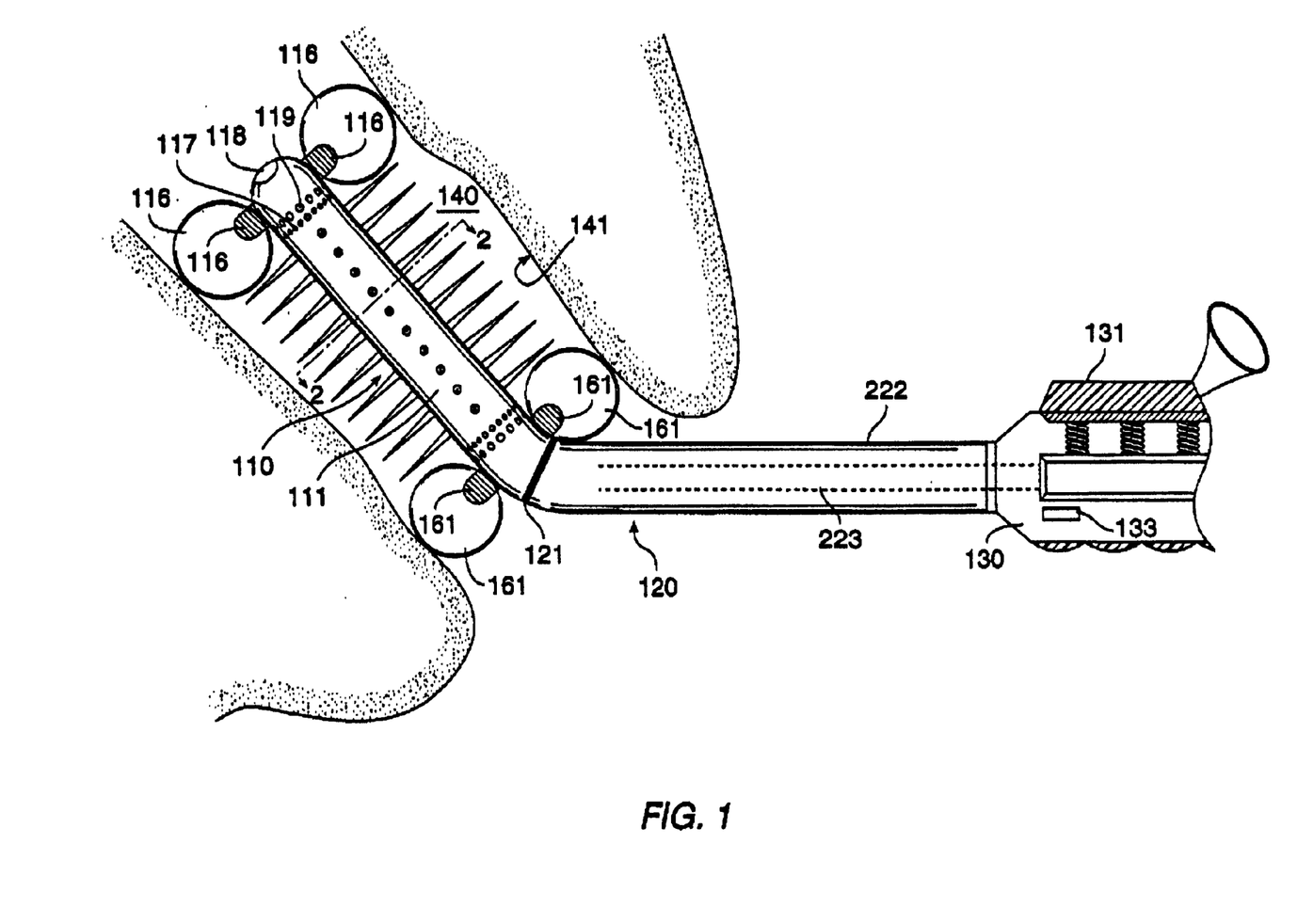
FIGS. 1 and 1a show a side view of a catheter and electrode assembly.
Figure 1A:
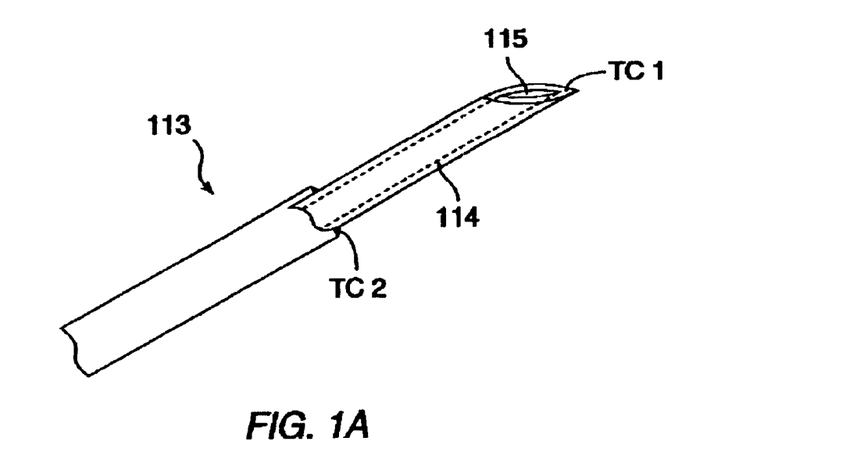

FIG. 1 shows a side view of a catheter and electrode assembly.

An assembly 100 for ablating rectal and other internal body structures includes a catheter 110, a control and delivery linkage 120, and a control element 130.

The catheter 110 is coupled to the control and delivery linkage 120 using a gearing element 121, which allows the catheter 110 to be rotated with respect to the control and delivery linkage 120 by an operator using the control element 130.

The catheter 110 includes a base 111, having a substantially cylindrical shape, coupled at a proximal end to the gearing element 121, and having a distal end. The catheter 110 is preferably disposed for insertion into the rectum at an angle to the control and delivery linkage 120, preferably an angle between about 30° and about 45° less than a right angle. The catheter 110 is between about 1 inch (2.54 cm) and about 2 inches (5.08 cm) in diameter, and between about 6 inches (15.24 cm) and about 8 inches (20.32 cm) in length.

The catheter 110 includes a plurality of holes 112, and a plurality of electrodes 113 which may be extended from at least some of the holes 112. The holes 112 are spaced regularly around the circumference and along the length of the catheter 110, having a spacing of about 0.25 inches (0.64 cm) between adjacent holes 112. The electrodes 113 are spaced regularly to occupy about one-half of the holes 112, and are between about 0.5 cm and about 1.0 cm in length.

The electrodes 113 each include a metallic tube 114 defining a hollow lumen 115, shaped similarly to an injection needle, so as to be disposed to deliver at least one flowable substance to a region 140 near the catheter 110. In a preferred embodiment, the deliverable flowable substance includes saline with a concentration of less than about 10% NaCl, which aids in both hydration of body structures and other tissue, and in delivery of RF energy to the region 140. However, in alternative embodiments, the deliverable flowable substance includes other substances, including saline with other concentrations, systemic or topical antibiotics, collagen or another hardenable substance, or other bioactive, chemoactive, or radioactive substances (including anesthetic, anti-inflammatory, or antispasmodic substances, or tracer materials).

The catheter 110 includes at least one balloon 116, disposed for inflation so as to block gas or fluid from the body from entering the region 140. In a preferred embodiment, there is a distal balloon 116 disposed at the distal end of the catheter 110 and there is a proximal balloon 116 disposed at the proximal end of the catheter 110. The distal balloon 116 and the proximal balloon 116 preferably each comprise ring-shaped balloons, disposed so that when inflated each surrounds the catheter 110 and makes a gas-tight or fluid-tight seal, both with the catheter 110 and with a wall 141 of the rectum or other body structure into which the catheter 110 is inserted. However, in alternative embodiments, the distal balloon 116 may comprise a spherical or ellipsoidal balloon disposed at the distal end of the catheter 110 in such manner that when inflated it surrounds the catheter 110 and makes a gas-tight or fluid-tight seal with the wall 141.

The catheter 110 also includes at least one balloon 116 disposed to anchor the catheter 110 at a selected location within the rectum or other body structure into which the catheter 110 is inserted. In a preferred embodiment, the balloon 116 used to anchor the catheter 110 is the proximal balloon 116, which when inflated prevents the catheter 110 from being expelled from the body in like manner as the operation of a Foley catheter. However, in alternative embodiments, the balloon 116 used to anchor the catheter 110 may comprise an additional or alternative balloon which is disposed solely or primarily for the purpose of anchoring the catheter 110 into its selected place, again in like manner as the operation of a Foley catheter.

The catheter 110 includes a fluid circulation system 117, including at least one fluid outlet port and at least one fluid inlet port. The fluid circulation system 117 is disposed for providing fluid in the region near the catheter 110, such as for delivering fluid for cooling the region 140 and for removing other fluid for aspirating the region 140.

The catheter 110 includes an optical view port 118, possibly including a lens or other transparent or translucent covering, disposed to allow inflow of light (visible or infrared) for transmission to an operator for viewing and control of the operation of the catheter 110.

The catheter 110 includes at least one sensor 119, such as a sensor 119 for impedance or temperature. In a preferred embodiment, the temperature sensor 119 includes a thermocouple, but in alternative embodiments, the temperature sensor 119 may include a thermistor or other device for sensing temperature and providing signals responsive to temperature near the catheter 110.

The control and delivery linkage 120 includes a metallic tube 223 defining a hollow lumen 224, and is further described with reference to FIG. 2.

In a preferred embodiment, the control and delivery linkage 120 is between about ½ inch (1.27 cm) and about ⅝ inches (1.59 cm) in diameter, and between about 6 inches (15.24 cm) and about 8 inches (20.32 cm) in length.

The control element 130 includes an electrode actuation element 131 for advancing the electrodes 113 out from the catheter 110, a electrode retraction element 132 for retracting the electrodes 113 into from the catheter 110, and an operation element 133 for controlling operation of the catheter 110, including delivery of flowable substances using the holes 112 and delivery of energy using the electrodes 113.

ADVANCING AND RETRACTING ELECTRODES

Figure 2:
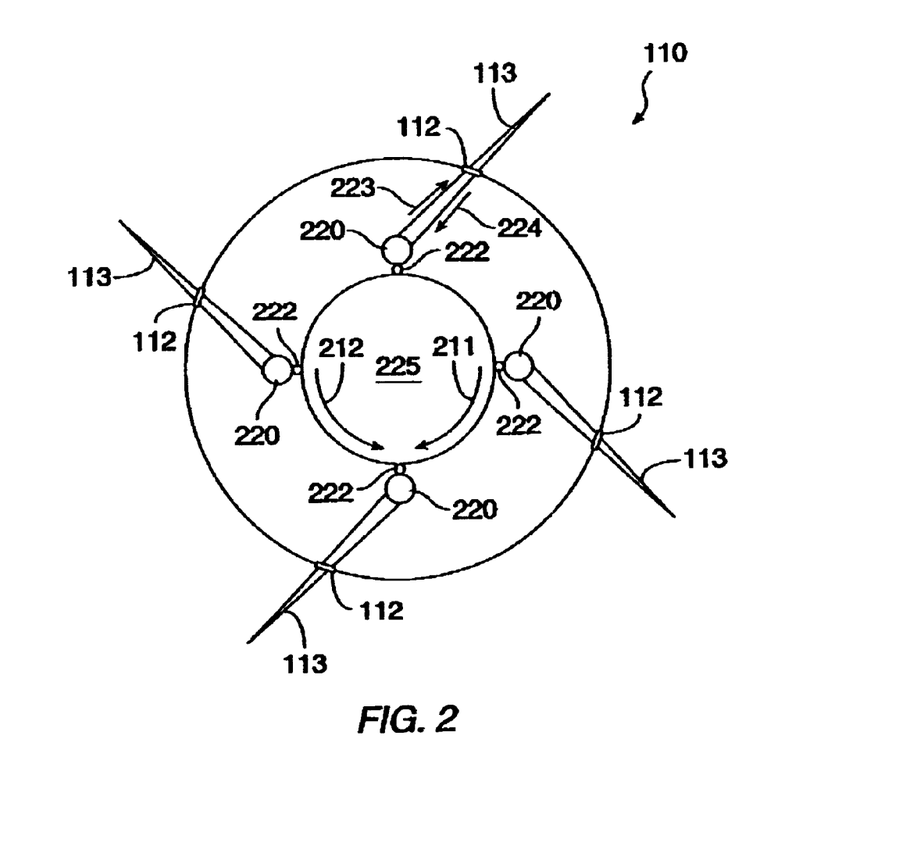
FIGS. 2 and 2a show a cut-away view of a catheter and electrode, taken along a line 2—2 in FIG. 1.
Figure 2A:
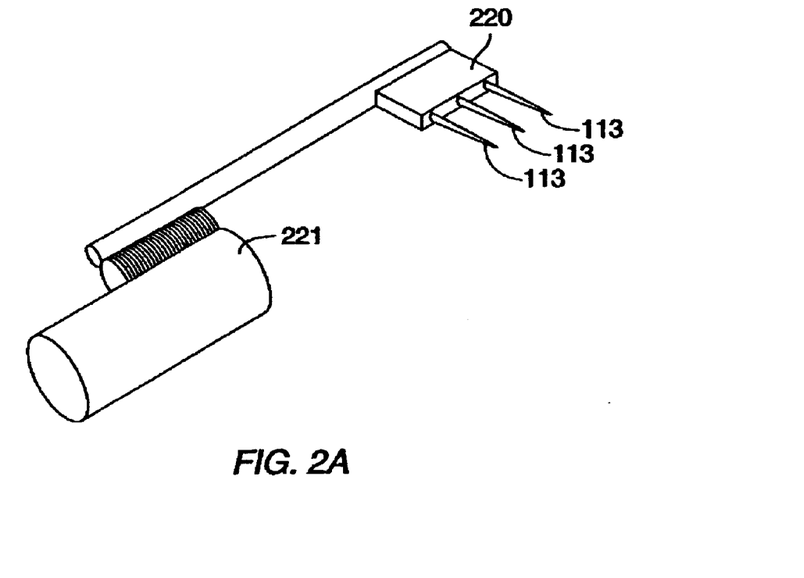

FIG. 2 shows a cut-away view of a catheter, taken along a line 2—2 in FIG. 1.

The catheter 110 comprises a rotatable element 210 which is disposed for rotation in a first direction 211 to advance the electrodes 113 out of the catheter 110 and in a second direction 212 opposite the first direction 211 to retract the electrodes 113 back into the catheter 110.

In a preferred embodiment, the rotatable element 210 is coupled to a spring (not shown) or other device which holds the rotatable element 210 in a steady state with the electrodes 113 retracted into the catheter 110.

The rotatable element 210 is coupled to the electrode actuation element 131, which forces the rotatable element 210 to rotate in the first direction 211 so as to advance the electrodes 113 out of the catheter 110. When the actuator element is not actuated, the spring causes the rotatable element 210 to rotate in the second direction 212 so as to retract the electrodes 113 back into the catheter 110.

Each electrode 113 is coupled to an electrode carrier 220. In a preferred embodiment, each electrode carrier 220 is substantially bar-shaped (but is shown end-on in the figure) and is coupled to a plurality of electrodes 113, such as about between about three and about six electrodes 113, so as to substantially simultaneously advance that plurality of electrodes 113 out of the catheter 110 and retract that plurality of electrodes 113 back into the catheter. A plurality of electrode carriers 220 are each disposed in a set of lines corresponding to lines of electrodes 113 disposed for advancement out of the catheter 110 and retraction back into the catheter 110.

In a preferred embodiment, the electrodes 113 may be disposed so that when advanced, the electrodes 113 extend to selected depths within the body structure to be ablated. These selected depths may be the same depth for all electrodes 113 which are advanced, or may include a first depth for a first set of electrodes 113 and a second depth for a second set of electrodes 113.

In a preferred embodiment, the electrode carriers 220 are coupled to a set of controls (not shown) in the control element 130 for selecting one or more electrode carriers 220 independently using one or more actuation levers 221, so as to be able to independently advance one or more sets of electrodes 113 coupled thereto out of the catheter 110 and to independently retract one or more sets of electrodes 113 back into the catheter 110.

Each electrode carrier 220 is coupled to the rotatable element 210 using a bearing 222, in such manner so as to translate rotation of the rotatable element 210 into linear radial movement of the electrodes 113. When the rotatable element 210 is rotated in the first direction 211, the electrodes are advanced in a first linear movement 223, while when the rotatable element 210 is rotated in the second direction 212, the electrodes are retracted in a second linear movement 224.

An interior 230 of the rotatable element 210 includes a lumen 225 through which fluids and other flowable substances are provided, and in which conductors providing control signals and sensor signals are disposed.

Operation of the Catheter and Electrode Assembly

Operation of the catheter and electrode assembly 100 includes at least the following steps:

The catheter 110 is inserted into the body at an opening, such as the rectum.

In a preferred embodiment, the opening is the rectum. A region of the rectum is first infused with a lubricant, such as K-Y jelly, and with an anesthetic, such as lidocaine. An anti-inflammatory, antispasmodic, or other condign medication would also be applied as appropriate. Thereafter, the catheter 110 is inserted into the lubricated region of the rectum. Due to the potential pain induced by the presence of the catheter 110 or electrodes 113, during operation the catheter 110 infuses a mixture of saline and lidocaine into the region 140 to be ablated.

In alternative embodiments, the opening may be another opening into the body, such as a natural orifice such as the vagina or the urethra, or an opening which has been made surgically, such as an incision which allows the catheter 110 to be inserted into a blood vessel.

The preferred size of the catheter 110 will of course be responsive to the size of the opening if other than the rectum. The choice of medicinal elements to be infused prior to or coeval with the catheter 110 will of course be responsive to judgments by medical personnel, and may include lubricants, anesthetics, antispasmodics, anti-inflammatories, antibiotics, or other materials with bioactive, chemoactive, or radioactive effect.

The catheter 110 is positioned within the body at a selected orientation and location, such as a position near a hemorrhoid.

Figure 3:
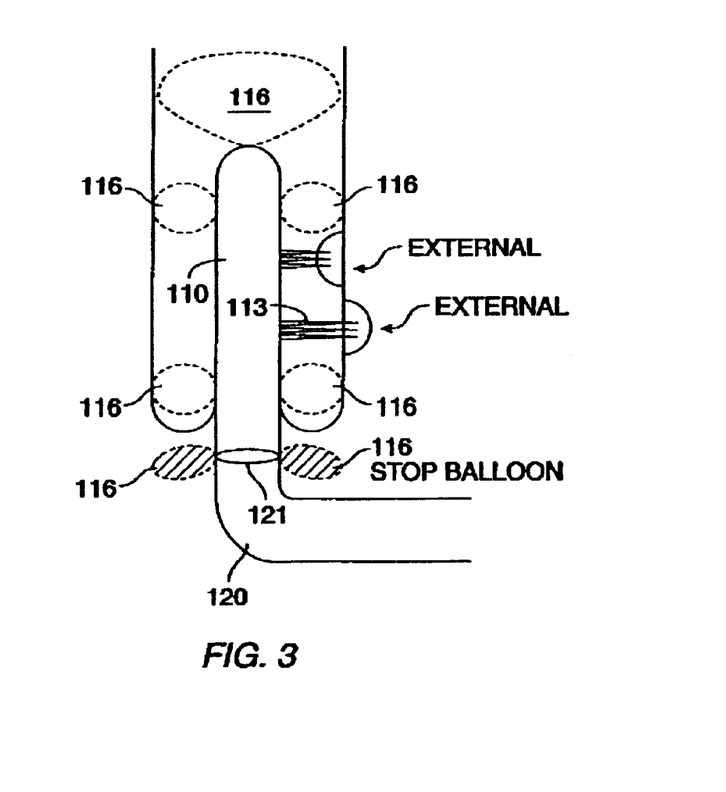
FIG. 3 shows a method of treatment of a hemorrhoid.

In one preferred embodiment, the catheter 110 is positioned in the rectum near an eternal or internal hemorrhoid, in a manner as shown in FIG. 3. In this preferred embodiment, the electrodes 113 are ultimately advanced into the hemorrhoid to ablate the hemorrhoid.

Figure 4:
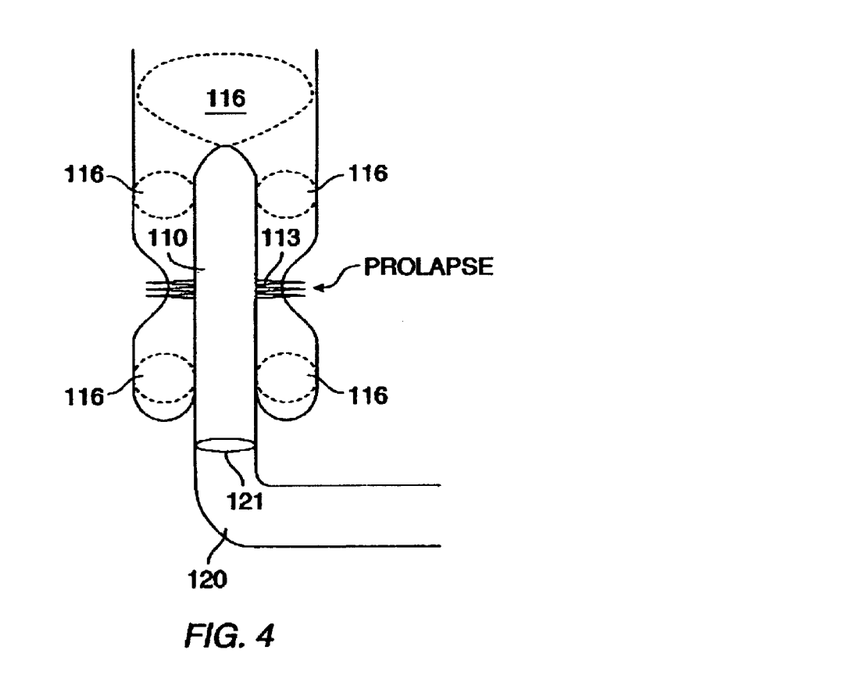
FIG. 4 shows a method of treatment of a prolapsed or spasmodic muscle.

In another preferred embodiment, the catheter 110 is positioned in the rectum near a prolapsed or spasmodic muscle, in a manner as shown in FIG. 4. In this preferred embodiment, the electrodes 113 are ultimately advanced into the prolapsed or spasmodic muscle to ablate selected portions of the prolapsed or spasmodic muscle.

Figure 5:
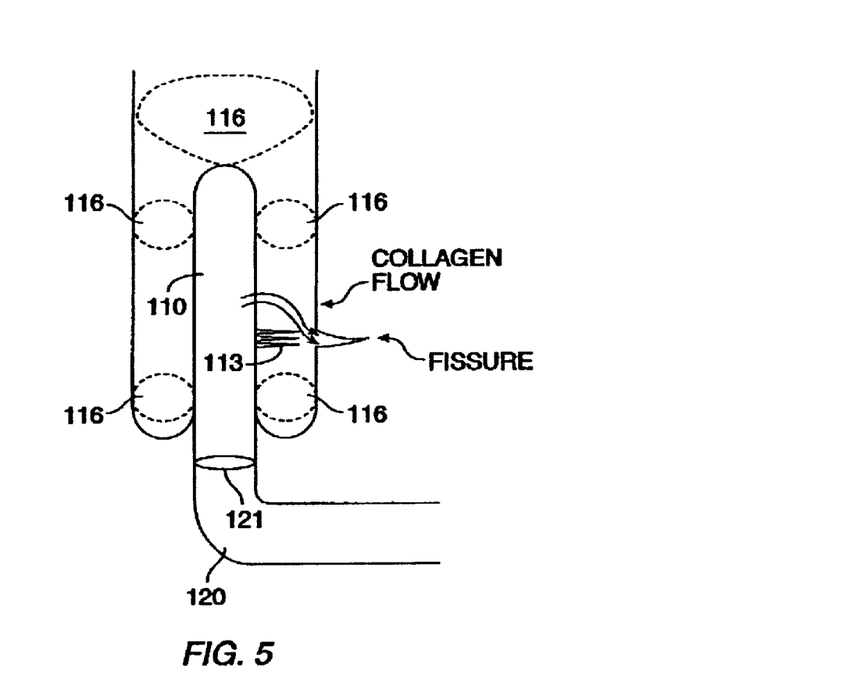
FIG. 5 shows a method of treatment of an anal fissure.

In another preferred embodiment, the catheter 110 is positioned in the rectum near an anal fissure, in a manner as shown in FIG. 5. In this preferred embodiment, collagen is deposited into the fissure and the electrodes 113 are ultimately advanced into a region near the collagen to harden the collagen for filling the fissure.

In another preferred embodiment, the catheter 110 is positioned in the colon near a polyp, in a manner similar to that shown in FIG. 3. In this preferred embodiment, the electrodes 113 are ultimately advanced into the polyp to ablate the polyp.

In another preferred embodiment, the catheter 110 is positioned in the rectum near a pilonital cyst, in a manner similar to that shown in FIG. 3. In this preferred embodiment, the electrodes 113 are ultimately advanced into the cyst to ablate the cyst.

In another preferred embodiment, the catheter 110 is positioned in the rectum, colon, large intestine, or small intestine, near a cyst or tumor, in a manner similar to that shown in FIG. 3. In this preferred embodiment, the electrodes 113 are ultimately advanced into the cyst or tumor to ablate the cyst or tumor.

Figure 6:
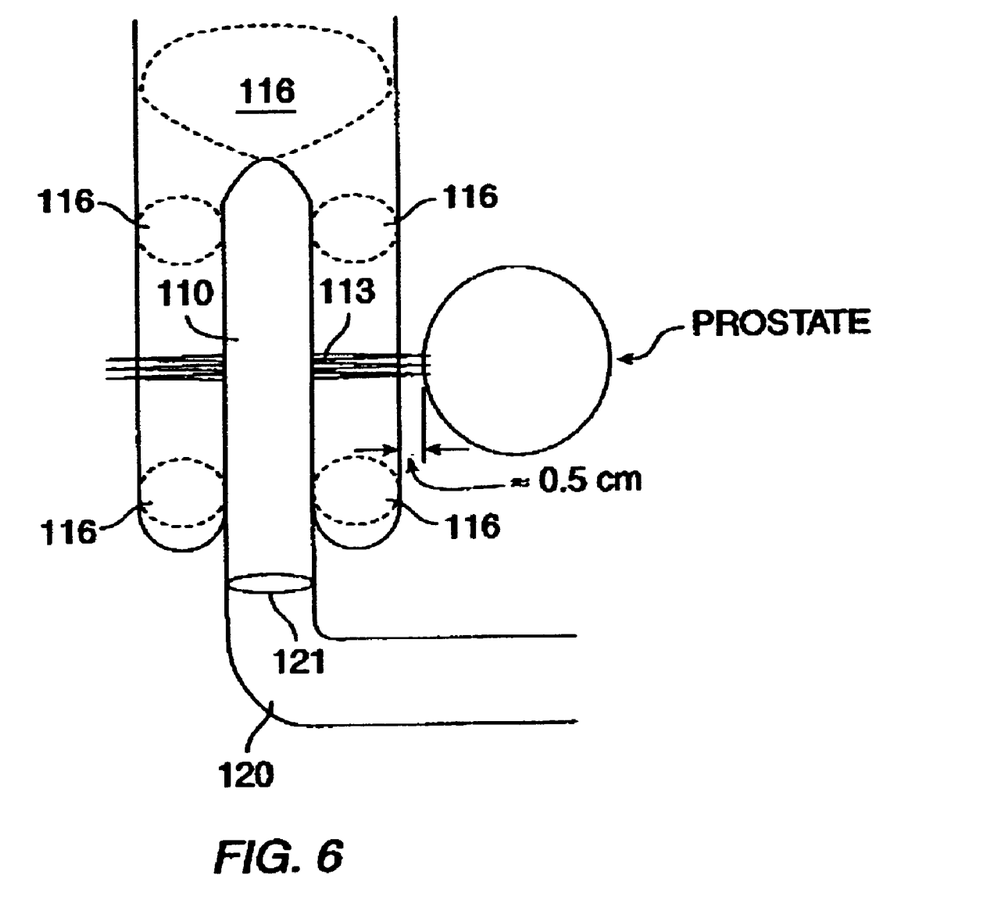
FIG. 6 shows a method of treatment of a tumor in the prostate.

In another preferred embodiment, the catheter 110 is positioned in a male patient, in the rectum near the prostate, in a manner as shown in FIG. 6. In this preferred embodiment, the electrodes 113 are ultimately advanced into a tumor in the prostate to ablate the tumor.

In another preferred embodiment, the catheter 110 is positioned in a female patient, in the vagina, near a cyst or fibroid, in a manner similar to that shown in FIG. 3. In this preferred embodiment, the electrodes 113 are ultimately advanced into the cyst or fibroid to ablate the cyst or fibroid.

In another preferred embodiment, the catheter 110 is positioned in a female patient, in the vagina, near a prolapsed uterus, in a manner similar to that shown in FIG. 4. In this preferred embodiment, the electrodes 113 are ultimately advanced into the prolapsed uterus selected portions of the prolapsed uterus.

The catheter 110 is anchored into place at the selected orientation and location by inflating a balloon 116, such as the distal balloon 116 and the proximal balloon 116.

In embodiments where the catheter 110 is positioned in the rectum, the catheter 110 is anchored into place using the proximal balloon 116 and the proximal balloon 116 operates in similar manner as a Foley catheter.

In alternative embodiments, the catheter 110 includes a stop balloon 116, such as a ring balloon (as shown in FIG. 3), disposed outside the body so as to prevent the catheter 110 from being inserted "too far", i.e., beyond its selected location.

The region 140 near the catheter 110 is isolated from the rest of the body by inflating the distal balloon 116 and the proximal balloon 116. In a preferred embodiment, this step uses the same distal balloon 116 and the proximal balloon 116 as the step of anchoring the catheter 110 into place.

Isolation of the region 140 near the catheter 110 from the rest of the body need not be absolute. In a preferred embodiment, the distal balloon 116 and the proximal balloon 116 are microporous, are inflated using saline or water, and thus are disposed to provide saline or water into the region 140 near the catheter 110. However, in such an embodiment, gas and fluids from the rest of the body are allowed to leak into one or more of the balloons 116 and from there are allowed to leak into the region 140 near the catheter 110.

Moreover, while in a preferred embodiment the seal made with the wall 141 of the region 140 by the balloon 116 is gastight, in alternative embodiments, that seal is allowed to be simply fluid-tight, and might allow gas to leak from the rest of the body into the region 140 near the catheter 110.

One or more sets of electrodes 113 are selected for advancement into a selected mass of tissue in the region 140. The rotatable element 210 is rotated in the first direction 211, causing the selected sets of electrodes 113 to advance out of the catheter 110 and into the selected mass of tissue.

The selected set of electrodes 113 are just those electrodes 113 which are needed to penetrate the selected mass of tissue for ablation.

In a preferred embodiment where the selected mass of tissue for ablation is a hemorrhoid, the selected set of electrodes 113 are just those electrodes 113 which are needed to penetrate the hemorrhoid. If a plurality of hemorrhoids are selected for ablation, either (1) electrodes 113 needed to penetrate the plurality of hemorrhoids are selected, or (2) electrodes 113 needed to penetrate one of the hemorrhoids are selected, and the operation is repeated for each individual one of the hemorrhoids.

Similarly, in preferred embodiments where the selected body structure for ablation is an individual cyst, fibroid, polyp, or tumor, the selected set of electrodes 113 are just those electrodes 113 which are needed to penetrate the selected body structure. If there is more than one such selected body structure, either (1) more than one set of electrodes 113 may be selected, or (2) just one set of electrodes 113 may be selected and the operation is repeated for each individual such body structure.

Similarly, in preferred embodiments where the selected body structure for ablation is muscle tissue or other tissue which is part of a larger body structure, such as a prolapsed or spasmodic muscle, the selected set of electrodes 113 are just those one or more sets of electrodes 113 which are needed to penetrate the portion of the body structure which has been selected for ablation.

Flowable substances are provided using the holes 112, and energy is provided to the electrodes 113, so as to ablate the mass of tissue in the region 140.

In a preferred embodiment, the flowable substances are provided using the holes 112 to the region 140 near the catheter In alternative embodiments, the flowable substances may be provided, in addition or instead, (1) from an area of the catheter covered by a microporous membrane, or (2) from one or more microporous balloons. The microporous balloons may either be the same as or in addition to the balloons 116 used to anchor the catheter in place or to block gas or fluid.

In preferred embodiments, the flowable substances have one of the following functions: (1) to aid in ablation, such as by transmitting RF energy from the electrodes 113 to the body structure to be ablated, as is done by saline or other electrolytic solutions, (2) to rehydrate tissue, as in done by saline or water, or (3) to repair tissue, such as by flowing into cysts or fissures or voids, or by covering lesions, as is done by collagen in a soft form which can be hardened by RF energy.

In a preferred embodiment, the electrodes 113 deliver RF energy having a frequency between about 435 megahertz and about 485 megahertz, for a period between about 5 minutes and about 10 minutes. The RF energy is received by and heats tissue and other body structures near the electrodes 113, causing ablation by means of cell death, dehydration, or denaturation.

In alternative embodiments, the electrodes 113 may deliver other forms of energy, such as heat, microwaves, or infrared or visible laser energy.

The electrodes 113 are controlled by a feedback technique, using the at least one sensor 119. In embodiments where there is more than one sensor 119, the feedback technique may be responsive to each sensor 119.

In one preferred embodiment, the at least one sensor 119 includes a temperature sensor 119 and the feedback technique includes a microprocessor (not shown) disposed in or coupled to the control element 130 and operating under control of application software for maintaining the temperature of the body structure to be ablated at a selected temperature, such as a temperature exceeding between about 90° Celsius and about 120° Celsius.

In this preferred embodiment, the microprocessor also controls delivery of fluids for cooling or hydration, so as to maintain the temperature of surrounding tissue (i.e., other than the tissue selected for ablation) at temperatures less than between about 90° Celsius and about 120° Celsius.

In another preferred embodiment, the at least one sensor 119 also includes an impedance sensor 119 and the feedback technique includes a microprocessor operating to terminate delivery of RF energy when a measured impedance of the body structure to be ablated undergoes a substantial change indicative of dehydration or denaturation.

One or more sets of electrodes 113 are selected for retraction back from the selected mass of tissue in the region 140. The rotatable element 210 is rotated in the second direction 211, causing the selected sets of electrodes 113 to retract out of the selected mass of tissue and back into the catheter 110.

The same electrodes 113 which were advanced out of the catheter 110 are retracted back into the catheter 110.

The catheter 110 is withdrawn from the body at the opening through which it was inserted.

Before removal, the balloons 116 are deflated so the catheter 110 is no longer anchored in place, all electrodes 113 are retracted back into the catheter 110, and the catheter 113 is configured to no longer provide flowable substances or energy for ablation.

PARTICULAR METHODS AND APPARATUS FOR TREATMENTS

In preferred embodiments, the catheter and electrode assembly 100 may also be used for treatments in addition to, or instead of, ablation of body structures or tissue.

In one preferred embodiment, operation of the catheter and electrode assembly 100 includes at least the following steps:

The catheter 110 is inserted into a natural body lumen, such as the urethra.

In a preferred embodiment, the natural body lumen comprises a normally tubular body structure which has prolapsed, is spasmodic, or is otherwise subject to blockage (partial or complete) or damage (such as to a wall of the natural body lumen).

The catheter 110 infuses a hardenable substance into the natural body lumen, so as to coat at least one selected section of the wall of the natural body lumen.

In a preferred embodiment, the hardenable substance includes a collagen which is capable of being flowed onto the wall of the natural body lumen and which is capable of being hardened by application of RF energy, heat, or another agent to be provided by the catheter and electrode assembly 100.

The electrodes 113 are advanced and deliver energy to the hardenable substance to harden it.

In a preferred embodiment, the holes 112 provide saline and the electrodes 113 deliver RF energy to the collagen to harden it, so as to form a hard covering to the wall of the natural body lumen. If appropriate, more than one layer of collagen is applied, so as to provide a hard covering having a thickness exceeding a selected threshold, such as 0.1 inch (0.25 cm). The particular selected threshold will of course depend on the preferred diameter of the natural body lumen.

In a preferred embodiment for treatment of a prolapsed or spasmodic muscle, (1) the catheter 110 is inserted and pushed through a region where the muscle has prolapsed or blocked the rectum, colon, large intestine, or small intestine, (2) the prolapsed or spasmodic muscle is partially ablated, and (3) collagen is infused and hardened to strengthen the muscle wall. In alternative embodiments, the collagen may be infused before ablation in one or more boluses deposited within the muscle (or on the muscle or near the muscle), so that the steps of muscle ablation and collagen hardening will occur substantially simultaneously.

In a preferred embodiment for treatment of an anal fissure, (1) the catheter 110 is inserted into a region where the 29 fissure has occurred, (2) a suspension of collagen and saline is infused and fills the fissure, and (3) the collagen is hardened while the saline is removed from the suspension. In this preferred embodiment, the isolated region between the distal balloon 116 and the proximal balloon 116 is maintained at a positive differential pressure with respect to the rest of the rectum, so that the collagen infuses into the fissure; this procedure or a similar procedure is also followed for treatment of diverticulosus and diverticulitis.

In a preferred embodiment for treatment, in a female patient, of a prolapsed uterus, (1) the catheter 110 is inserted into a region where the uterus has prolapsed, (2) the prolapsed uterus is partially ablated, and (3) collagen is infused and hardened to strengthen the muscle wall. Similarly to treatment of a prolapsed muscle, in alternative embodiments, the collagen may be infused before ablation, so that the steps of muscle ablation and collagen hardening will occur substantially simultaneously.

Alternative Embodiments

Although preferred embodiments are disclosed herein, many variations are possible which remain within the concept, scope, and spirit of the invention, and these variations would become clear to those skilled in the art after perusal of this application.

We claim:

1. Apparatus for ablating a structure in a region within a body, said apparatus including:
   a catheter disposed for positioning in said region;
   means for isolating said region from gas or fluid from outside said region;
   an electrode coupled to said catheter such that rotation of a control element coupled to said catheter is translated to linear movement of said electrode; and
   means for aspirating fluid from said region.

2. Apparatus as in claim 1, wherein said region is in or near the sphincter, rectum, colon, or prostate.

3. Apparatus as in claim 1, wherein said structure includes a cyst, hemorrhoid, polyp, tumor, or lesion.

4. Apparatus as in claim 1, wherein said energy. includes RF energy having a frequency between about 435 megahertz and about 485 megahertz.

5. Apparatus as in claim 1, including means for advancing said electrode from within said catheter to a point inside a selected mass of tissue within said region.

6. Apparatus as in claim 1, wherein said means for isolating includes at least one balloon.

7. Apparatus as in claim 6, wherein said at least one balloon includes a balloon disposed at an upstream location or disposed at a downstream locations from said region.

8. Apparatus as in claim 6, including means for inflating said at least one balloon.

9. Apparatus as in claim 6, wherein said at least one balloon is operative to anchor said catheter in a selected location.

10. Apparatus as in claim 1, including means for anchoring said catheter in a selected location.

11. Apparatus as in claim 10, wherein said means for anchoring includes at least one balloon capable of being disposed against a wall of said region.

12. Apparatus as in claim 1, including
   at least one control parameter sensor; and
   means, responsive to said control parameter sensor, for controlling said electrode.

13. Apparatus as in claim 1, including means for delivering a flowable substance to said region.

14. Apparatus as in claim 13, including
   at least one control parameter sensor; and
   means, responsive to said control parameter sensor, for controlling said means for delivering.

15. Apparatus as in claim 13, wherein said flowable substance includes an effective amount of fluid to cool said region to a selected temperature.

16. Apparatus as in claim 13, wherein said flowable substance includes an effective amount of fluid to rehydrate a selected mass of tissue in said region.

17. Apparatus as in claim 13, wherein said flowable substance includes saline.

18. Apparatus as in claim 13, wherein said flowable substance includes an antibiotic.

19. Apparatus as in claim 13, wherein said flowable substance includes collagen.

20. Apparatus as in claim 13, wherein said flowable substance includes a substance for covering or filling a selected structure within said region.

21. Apparatus as in claim 13, wherein said means for delivering includes at least one hole in said catheter.

22. Apparatus as in claim 13, wherein said means for delivering includes a microporous membrane.

23. Apparatus as in claim 13, wherein said means for delivering includes a balloon having a microporous membrane.

24. Apparatus as in claim 1, including an optical path from said region to a point outside the body, whereby an operator is able to view said region.

25. Apparatus as in claim 24, including means for controlling an orientation or position of said catheter responsive to said view.

26. Apparatus as in claim 24, including a view piece coupled to said optical path.

27. Apparatus as in claim 1, wherein said region is in or near a ligament, bone or cartilage.

28. Apparatus for treatment of a sphincter in a body, comprising:

a catheter;

a source of RF energy coupled to said catheter;

means for disposing said catheter in a region of said body near said sphincter;

an electrode for delivering said RF energy from said catheter to a tissue of said sphincter in an amount effective to treat said tissue, said electrode coupled to said catheter such that rotation of a control element coupled to said catheter is translated to linear movement of said electrode; and means for aspirating fluid from said region.

29. An apparatus as in claim 28, wherein said sphincter is a lower esophogeal sphincter, a GI sphincter, a rectum, a colon, a blood vessel, an organ, a urethra, a vagina, a prostate.

30. An apparatus as in claim 28, wherein at least a portion of said region is a cavity in said body.

31. An apparatus as in claim 30, wherein said cavity is an element of a gastrointestinal tract, a vascular system, a circulatory tract, a uro-genital tract, a pulmonary system, a lymphatic tract, or an organ.

32. An apparatus as in claim 28, wherein at least a portion of said tissue is an esophogeal varice, a hemorrhoid, a cyst, a polyp, a tumor, or a lesion.

33. An apparatus as in claim 28, wherein said effective amount of RF is effective to heat at least a portion of said tissue, to ablate at least a portion of said tissue, to destroy at least a portion of said tissue, or to contract at least a portion of said tissue.

34. An apparatus as in claim 28, including:

a substance effective for treatment of said tissue;

means for providing said substance from a source coupled to said catheter; and means for delivering said substance from said catheter to said tissue in an amount effective to treat at least a portion of said tissue.

35. An apparatus as in claim 34, wherein said substance comprises a flowable substance, a medicament, a saline solution, an astringent, a collagenous fluid or other bulking agent, a bio-active substance, a chemo-active substance, a radioactive substance, or a sclerosing agent.

36. An apparatus as in claim 28, wherein said means for delivering said effective amount RF energy comprises an electrode disposed on said catheter.

37. An apparatus as in claim 36, wherein said electrode comprises one or more of the following: a curvilinear hollow needle disposed for advancing out of said catheter and penetrating a portion of said tissue, a monopolar ring electrode, a pair of bipolar ring electrodes, or a pair of bipolar electrodes disposed for direct contact with a portion of said tissue.

38. An apparatus as in claim 28, including means for delivering near said sphincter a substance effective to treat at least a portion of said tissue.

39. An apparatus as in claim 38, wherein said substance includes one or more of the following: a flowable substance, a medicament, a saline solution, an astringent, a collagenous fluid or other bulking agent, a bio-active substance, a chemo-active substance.

40. An apparatus as in claim 30, wherein said cavity is an element of a ligament, bone or cartilage.

* * * * *